United States Patent
Majewski et al.

(10) Patent No.: US 10,634,747 B2
(45) Date of Patent: Apr. 28, 2020

(54) APPARATUS AND IMPLEMENTATION METHOD OF A SET OF UNIVERSAL COMPACT PORTABLE MR-COMPATIBLE PET INSERTS TO CONVERT WHOLE-BODY MRI SCANNERS INTO ORGAN-SPECIFIC HYBRID PET/MRI IMAGERS

(71) Applicant: West Virginia University, Morgantown, WV (US)

(72) Inventors: Stanislaw Majewski, Morgantown, WV (US); James Proffitt, Newport News, VA (US); James Lewis, Morgantown, WV (US); Julie Brefczynski-Lewis, Morgantown, WV (US); Alexander Stolin, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 36 days.

(21) Appl. No.: 13/827,557

(22) Filed: Mar. 14, 2013

(65) Prior Publication Data

US 2014/0275965 A1 Sep. 18, 2014

(51) Int. Cl.
 *G01R 33/48* (2006.01)
 *G01T 1/29* (2006.01)
 *G01T 1/16* (2006.01)

(52) U.S. Cl.
 CPC .......... *G01R 33/481* (2013.01); *G01T 1/1603* (2013.01); *G01T 1/2985* (2013.01)

(58) Field of Classification Search
 CPC .................................................. G01R 33/481
 See application file for complete search history.

(56) References Cited

U.S. PATENT DOCUMENTS

| 7,884,331 B2 | 2/2011 | Majewski et al. |
| 2010/0187424 A1* | 7/2010 | Majewski et al. ....... 250/363.05 |

(Continued)

OTHER PUBLICATIONS

Kang et al., "A feasibility study of photosensor charge signal transmission to preamplifier using long cable for development of hybrid PET-MRI", Nov. 2010, Medical Physics, vol. 37, No. 11, p. 5655-5664.*

(Continued)

*Primary Examiner* — Carolyn A Pehlke
*Assistant Examiner* — Marjan Saboktakin
(74) *Attorney, Agent, or Firm* — Buchanan Ingersoll & Rooney PC; Craig G. Cochenour, Esq.

(57) ABSTRACT

A Positron Emission Tomography ("PET") insert for use with a Magnetic Resonance Imaging ("MRI") scanning device, the PET insert including a plurality of photodetector modules provided adjacent each other in an array, the plurality of photodetector modules configured for placement adjacent a body of a patient and sized to be received in a magnetic bore of the MRI scanning device with the patient, the photodetector modules providing detection of gamma annihilation photons, and a Radio Frequency ("RF") coil provided between the patient and the plurality of photodetector modules. Each of the plurality of photodetector modules includes a pixelated scintillator array provided for alignment adjacent the patient's body, and a shielding block including silicon photomultiplier pads and passive electronic circuitry only.

19 Claims, 14 Drawing Sheets

(56) References Cited

U.S. PATENT DOCUMENTS

2011/0224534 A1* 9/2011 Yamaya et al. .............. 600/411
2012/0136237 A1* 5/2012 Benlloch Baviera .. A61B 5/055
                                                        600/411

OTHER PUBLICATIONS

Schlemmer et al., "Simultaneous MR/PET Imaging of the Human Brain: Feasibility Study", Sep. 2008, Radiology, vol. 248, No. 3, p. 1028-1035.*

"Analog signal multiplexing for PSAPD-based PET detectors: simulation and experimental validation", Lau et al, Phys. Med. Biol. 2010.*

Zang-Hee C, et al., "A Hybrid PET-MRI: An Integrated Molecular-genetic Imaging System with HRRT-PET and 7.0-T MRI," Int'l J Imaging Sys Tech 2007; 17:252-65.

Lucas AJ, et al., "Development of a Combined MicroPET-MR System," Technol Cancer Res Treat 2006; 5:337-41 Abstract Only.

Handler W, et al., "Combining Field-Cycled Magnetic Resonance Imaging with Positron Emission Tomography (abstract)," J Nucl Med Meeting Abstracts 2007; 48(Suppl 2):89P.

http://www.diagnosticimaging.com/pet-mr/content/article/113619/2040136.

Nishikido F., et al., "Feasibility Study for a PET Detector Integrated with an RF Coil for PET-MRI," presented at and in the conference record of the 2011 IEEE Medical Imaging Conference, Oct. 23-29, 2011, Valencia, Spain.

Hong K.J., et al., "Performance Evaluation of a PET Detector Consists of a LYSO array coupled to a 4×4 array of large-size GAPD for MR Compatible Imaging," J Instrum., vol. 6, P05012, 2011.

Kang J., et al., "A Feasibility Study of Photosensor Charge Signal Transmission to Preamplifier Using Long Cable for Development of Hybrid PET-MRI," Med. Phys., vol. 37, pp. 5655-5664, 2010.

Jung J.H., et al., "Development of a Position Decoder Circiut for PET Consisting of GAPD Arrays," Nucl. Instr. and Meth., vol. A 621, pp. 310-315, 2010.

Hu W., et al., "A Simple and Improved Digital Timing Method for Positron Emission Tomography," Nucl. Instr. and Meth., vol. A 622, pp. 219-224, 2010.

* cited by examiner

FIGURE 5
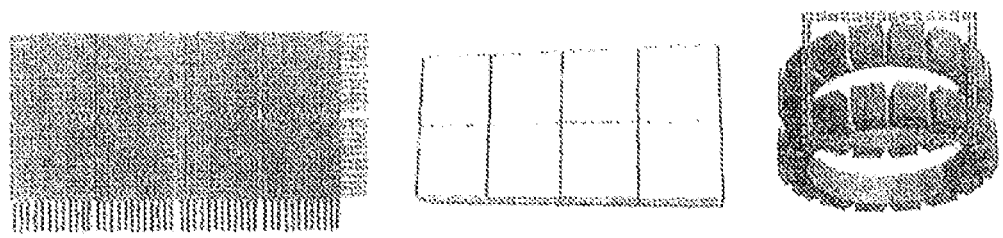
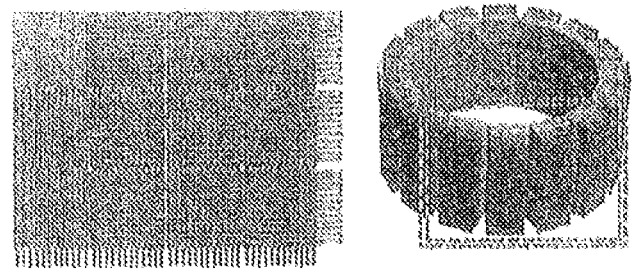
FIGURE 6

APPARATUS AND IMPLEMENTATION METHOD OF A SET OF UNIVERSAL COMPACT PORTABLE MR-COMPATIBLE PET INSERTS TO CONVERT WHOLE-BODY MRI SCANNERS INTO ORGAN-SPECIFIC HYBRID PET/MRI IMAGERS

STATEMENT REGARDING FEDERALLY SPONSORED RESEARCH/DEVELOPMENT

This invention was made with government support under Grant No. P30GM103503 awarded by the National Institute of Health. The government has certain rights in this invention.

FIELD OF THE INVENTION

The present disclosure is generally directed toward a combination of Position Emission Tomography ("PET") and Magnetic Resonance Imaging ("MRI") system technologies and, more particularly, toward hybrid PET-MRI imaging systems and methods and, even more particularly, towards systems and methods of providing MR-compatible PET inserts for converting whole-body MRI scanners into organ-specific PET/MRI imagers.

BACKGROUND OF THE INVENTION

Various groups around the world are working on the concept of PET/MRI imagers. They all use the enabling compact MRI-compatible solid-state technology in the PET detectors. The previous light sensor MRI-compatible technology implemented in the PET component was Avalanche Photo Diode ("APD"). A new whole body PET/MRI imager manufactured by mMR Siemens is using this technology. Most recently, research groups and companies are in the process of developing MRI-compatible PET systems based on the so-called Silicon Photomultiplier ("SiPM") photo sensor. SiPMs have many designs and many companies and research centers around the world are developing and producing them. For example, Hamamatsu, Japan and SensL, Ireland are examples of a few such entities. In addition, a Korean group at Sogang University in Seoul and a Japanese group at National Institute of Radiological Sciences ("NIRS"), Chiba, Japan, are also developing SiPM-based PET rings for brain imaging inside MRI.

There is a dramatic need for hybrid PET/MRI imaging with MRI providing the anatomical structural information and PET-molecular information about biological activity of the relevant tissues and organs. The only currently practical method to produce combined PET and MRI images is to obtain separate PET and MRI scans, which are executed on separate scanners, at different time slots. A combination of images from these two modalities provides the most powerful diagnostic tool. Acquiring MRI and PET images separately and then co-registering them is a complicated and expensive two-part imaging process. The co-registration of these images obtained at different times may, in some cases, result in relevant correlation information being lost between the times the two scans were performed. The cost of these two expensive imaging procedures is also high and adds up in a particular patient case. Currently, PET/MRI scanners are just entering the market; however, these scanners are complicated and very expensive (approximately $6-million), making it prohibitive for medical centers to acquire them. Accordingly, they will have limited availability to most patients for many years to come. It is proposed herein to provide an alternative, low-cost system and method, mostly (but not only) applicable to imaging of a particular organ, such as, but not limited to, brain, breast, head/neck, prostate, OB/GYN, heart, and other extremities, by the inventive implementation of PET inserts in any MRI scanner.

The present disclosure is directed toward overcoming one or more of the above-identified problems.

SUMMARY OF THE INVENTION

The technology outlined in this disclosure describes a hybrid PET/MRI imaging system and method. PET and MRI imaging are powerful imaging techniques used, for example, in biomedical research and clinical diagnostics. PET imaging, in combination with a radioactive tracer, provides molecular information about specific tissues and organs and enables the visualization of biological activity. Though incredibly sensitive, PET only provides physiological information and no anatomical information. Thus, PET is often used in combination with Computed Tomography ("CT") or MRI scans to obtain a more comprehensive anatomical and metabolic profile image. Both CT and MRI scans provide detailed information about the internal structures of the body. Often, PET scans are immediately followed by a CT or MRI scan, although more recently, a tandem PET/CT machine has been used in clinical imaging. Although PET/CT systems are useful, CT technology is not as sensitive as MRI data, especially in terms of soft tissue contrast data. Additionally, CT scans can expose the patient to higher radiation doses. Therefore, there is a clear need for a PET/MRI dual imaging system that can combine the advantages of both imaging systems.

The inventors herein have created a portable PET imager that is very compact and made to be MRI-compatible, so that it can operate as an insert inside the MRI scanners. In addition to operating as a compact PET imaging system, as a result of making the system to be compatible with MRI scanning, the inventors herein have thus creating a PET/MRI dual imaging system. In a first preferred embodiment the PET insert is in a form of a ring of individual detection modules that surround the patient's head. But the same ring can be used to image neck, breast, or other extremities. In a second embodiment, the PET insert is in the form of several planar—panel type—modules that operate in coincidence inside the MRI scanner. In another embodiment, the system can be comprised of a compact endorectal or surgical PET probe operating in coincidence with the panel modules. Such an embodiment is particularly useful for imaging the prostate gland and surrounding organs in a patient.

The approach of a single PET insert in MRI can be extended to a set of inserts to cover different parts of the body at the same time. The inserts can increase their coverage to larger regions of the patient's body, and can be offered as an upgrade option to operate with almost any MRI scanner.

In one implementation, the PET insert requires availability and proper installation of MRI model specific Radio Frequency ("RF") coils to minimize the interference of the PET insert (primarily, the impact is through the decreased signal to noise ratio of the MRI signal) on the MRI operation. In the best-case scenario, the standard, also flexible, RF coils provided with the MRI scanner will suffice. When operated with a whole body RF coil, some MRI imaging sequences may be impacted and cannot be used, while some may still provide sufficient quality images.

In some instances, a detailed evaluation of the compatibility of the PET insert(s) with the particular MRI scanner model needs to be performed. The optimal RF coil selection should be performed for each individual PET insert and MRI. Further, special case-specific RF coils may need to be implemented with each PET insert for a particular MRI model and mode of operation (e.g., imaging sequences) so as to minimize or eliminate interference effect of the PET insert on the MRI scanner operation.

Variations of the present invention can include more MRI-model specific PET inserts, as opposed to generic ones, operating, in principle, with any MRI scanner. In some models of the model-specific PET inserts, the MRI RF coils can be built into, or incorporated as part of, the structure of the PET insert. However, in this case, the flexibility of the inventive solution may be diminished. Careful balancing of the operational parameters versus the complexity and flexibility of this "upgrade" of an MRI scanner to a dedicated organ-specific (e.g., brain, breast, neck, extremity, prostate, OB/GYN, heart, etc.) PET/MRI scanner needs to be performed on a case by case basis, working with MRI scanner producers and the medical center customers.

The present invention offers various improvements and differentiators with respect to prior art techniques. Some of which include:

The PET ring of the present invention very tightly surrounds the patient's head, without a "stand-off" distance. For a long time, this gap distance was assumed to be necessary to assure proper operation of the PET reconstruction software. However, studies by the present inventors have proved that it is possible to get suitable performance without the gap distance once one carries out proper calibration of the imager response.

The present invention does not use specialized MRI RF coils, which are typically considered the standard and judged to be the necessary approach. In contrast, the present invention rather performs imaging with: (1) the whole body RF coil built into the MRI scanner; or (2) implementation of the standard flexible coils that are typically part of a set of coils delivered with the scanner and/or available from the MRI scanner manufacturer.

The inventive technical approach described herein is the consequence of the current inventors' general philosophy (against the common approach) that proposes to use the PET inserts that can be brought to operate inside practically any MRI scanner with only minimal necessary adaptation of the MRI imaging procedure to be able to produce hybrid PET/MRI images.

In accordance with the teaching of the present invention, almost any existing whole-body MRI scanner (with about 36,000 currently installed in the world) can be, at low cost and practically with no or minimal modifications/adaptations, converted into an organ-specific PET/MRI imager. The first focus that has been considered is PET/MRI brain imaging. But imaging of body parts and organs is also contemplated including, but not limited to, head/neck, breast, prostate, OB/GYN, heart, and other extremities, which are other envisaged applications.

A PET insert for use with an MRI scanning device is provided, the PET insert including a plurality of photodetector modules provided adjacent each other in an array, the plurality of photodetector modules configured for placement adjacent a body of a patient and sized to be received in a magnetic bore of the MRI scanning device with the patient, and the photodetector modules providing detection of gamma annihilation photons; and an RF coil provided between the patient and the plurality of photodetector modules. Each of the plurality of photodetector modules includes a pixelated scintillator array provided for alignment adjacent the patient's body, and a shielding block including silicon photomultiplier pads and passive electronic circuitry.

In one form, the plurality of photodetector modules is formed as a ring for provision about a body part of the patient. The RF coil is provided about at least part of an annular range of the photodetector module ring. The ring can include a plurality of rings stacked on top of each other forming a cylinder. The ring can also include a plurality of rings, with at least some of the rings spaced apart from other rings for provision about different parts of a patient's body.

In another form, each shielding block includes passive electronic circuitry only, such that the active components of the PET insert are disposed outside of the magnetic bore of the MRI scanner.

In another form, the RF coil extends past the edges of the plurality of photodetectors. The RF coil can be a standard coil provided with the MRI scanner with which the PET insert is used, or can include a whole body RF coil.

In another form, the plurality of photodetector modules is formed as a panel having an N×M array of photodetector modules. For imaging, at least two PET panels are provided for provision against a patient's body in opposing relationship for imaging a desired portion of the patient's body. An endorectal PET probe operatively associated with the PET panel can be provided for imaging of, for example the prostate or vaginal regions.

In another form, the photodetector modules include a scintillator as a sensor and energy converter of 511 keV annihilation gamma rays, and a photodetector to detect scintillation light produced by the absorbed gamma rays in the scintillator.

In an alternate embodiment, a PET insert for use with an MRI scanning device is provided, the PET insert including a plurality of photodetector modules provided adjacent each other in an array and formed as a ring for provision around a portion of a patient's body, the photodetector module ring sized to be received in a magnetic bore of the MRI scanning device with the patient, the photodetector modules providing detection of gamma annihilation photons; and an RF coil provided between the patient and the plurality of photodetector modules. The RF coil is provided about at least part of an annular range of the photodetector module ring, and extends over the edges of the photodetector module ring. Each of the plurality of photodetector modules includes a pixelated scintillator array provided for alignment adjacent the patient's body, and a shielding block including silicon photomultiplier pads and passive electronic circuitry only.

In one form, the photodetector module ring includes a plurality of rings stacked on top of each other forming a cylinder.

In another form, the photodetector module ring includes a plurality of rings, at least some of the rings spaced apart from other rings for provision about different parts of a patient's body.

In a further embodiment, a PET insert for use with an MRI scanning device is provided, the PET insert including a plurality of photodetector modules provided adjacent each other in an array and formed as at least two panels for provision against a patient's body in opposing relationship for imaging a desired portion of the patient's body, the at least two photodetector module panels sized to be received in a magnetic bore of the MRI scanning device with the patient. The photodetector modules providing detection of gamma annihilation photons. An RF coil is provided between the patient and the plurality of photodetector modules of each of the at least two panels, wherein the RF coil extends over the edges of the at least two photodetector module panels. Each of the plurality of photodetector modules includes a pixelated scintillator array provided for alignment adjacent the patient's body, and a shielding block including silicon photomultiplier pads and passive electronic circuitry only.

In one form, each of the at least two panels has an N×M array of photodetector modules.

In another form, an endorectal PET probe is provided that is operatively associated with the at least two PET panels. Such a configuration has particularly utility for imaging the prostate and/or vaginal regions.

It is an object of the present disclosure to provide a universal set of organ-specific MR-compatible PET inserts allowing for wide-spread use of PET/MRI diagnostics.

Various other objects, aspects and advantages of the present disclosure can be obtained from a study of the specification, the drawings, and the appended claims.

BRIEF DESCRIPTION OF THE DRAWINGS

Further possible embodiment(s) are shown in the drawings. The present disclosure is explained in the following in greater detail with reference to exemplary embodiment(s) depicted in drawings. In the drawings:

FIG. 5 illustrates a 4×2 module panel in a two-ring PET insert;

FIG. 6 illustrates a 4×3 module panel in a three-ring PET insert;

DETAILED DESCRIPTION OF THE INVENTION

Figure 1:
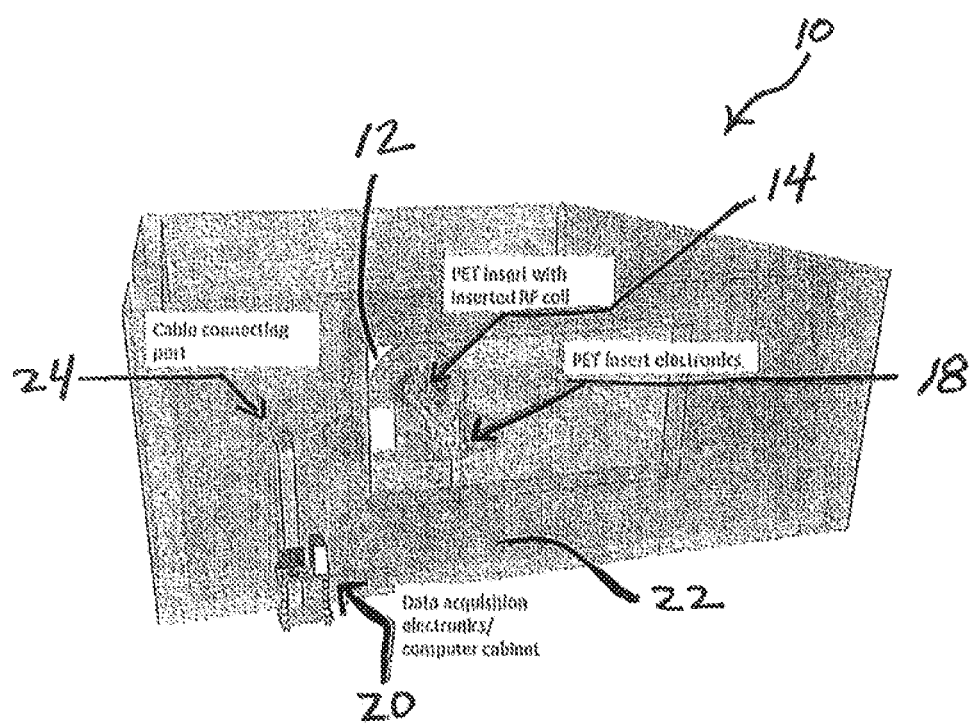
FIG. 1 illustrates an exemplary MRI scanning room environment for use with the PET inserts of the present invention.

Nuclear medicine imaging modalities (e.g., PET, single gamma, SPECT (Single-Photon Emission Computed Tomography)) are very powerful functional and molecular imaging diagnostic tools. However, they, as well as CT (Computer Tomography), are associated with the sensitive issue of radiation exposure to the patient by requiring radiation to be injected in the patient in the form of a radiolabeled imaging agent. In the case of CT, the source of radiation is external to the patient and the X-ray beam is sent through the patient's body with a large fraction of radiation being absorbed and, therefore, delivering a radiation dose to the patient's organs and tissue.

The issue of patient radiation exposure is often discussed not only in the medical community but also by the public, and every few months receives a lot of attention from the media, often due to another misapplication of diagnostic tests (e.g., CT), or on the occasion of new improvements of, and in stark comparison with, MRI and Ultrasound modalities. One can speculate how much such negative press coverage actually impacts the public's perception of the nuclear medicine based lifesaving tests, to the point that there is a tendency by the patients and, to some extent, by medical professionals, to limit application of these tests and/or to substitute them instead with MRI or Ultrasound ("US") scans. When used alone, both MRI and US modalities do not provide enough differentiating power for the accurate diagnosis of many diseases. This can result in a higher than desired number of false positives or fast negatives. For example, as a result, the opportunity of early cancer or neurological disease detection and proper staging can be compromised.

With the new PET insert approach of the present invention, it is possible to lower the injected or otherwise delivered radiation doses, while not compromising the quality of the task-specific diagnostic tests. Due to the latest technological developments in radiation detectors, it is believed that there is especially now, at this time, an opportunity to discuss and implement such measures. The special enabling detection technology of MRI-compatible Silicon Photomultipliers ("SiPMs") combined with the Time of Flight ("TOF") PET detector mode of operation makes it in principle possible to substantially increase the detection efficiency of the uptake signal in the organ(s) of interest at a lower injected dose of radiation. Additionally, there is the added benefit of combining MRI and PET at a never before reached availability level. In principle, every MRI scanner can be converted into a dedicated organ-specific PET/MRI imager by implementing, in accordance with the present invention, high performance and economical PET inserts inside the MRI scanner.

The possible methods that can lead to a decrease in the injected radioactive dose into the patient include, but are not limited to:

Increased detector efficiency (e.g., design, close geometry, etc.).
Better collimators (e.g., single gamma, SPECT, etc.).
Improvement in radio imaging agents (e.g., biology, specificity, uptake, etc.).
Optimization of reconstruction software and analytical algorithms.
Task-specific dose requirements as opposed to generic standard doses.
Indirectly, through dual modality imaging PET/MRI and SPECT/MRI with MRI modality, providing structural information (e.g., less demand on high resolution/high statistics in PET or SPECT images).

The best approach will depend on the interplay between the dose, specificity (due to biology) of the imaging agent, and detector efficiency and spatial resolution, on the one side, and imaging quality (e.g., S/N, contrast, etc.) on the other side, for different size structures of interest/lesions to detect and diagnose.

The specificity of the imaging agents is a critical component of the strategy on reduction the radioactive doses. Higher differentiation of uptake of imaging agent in diseased versus healthy organ or tissue can allow for lower doses while not compromising the above differentiation. However, the development of new imaging agents and the approval for their use in humans takes many years, while improvements in the detector technology could be implemented on a much shorter time scale.

The special technical subject is the issue of spatial resolution of the novel dedicated nuclear medicine imagers. At the two extremes are: at one end, the very high resolution systems offering 1 mm and even sub-mm spatial resolution (typical of the small animal imagers); and, on the other end, the "pattern" imagers when the demand for spatial resolution is not a major driver. An example for the requirement for high resolution is the use of PET in breast imaging or prostate imaging. The detection of Alzheimer's, on the other hand, is an example of the second "pattern" category, where 4 mm or even 8 mm resolution may be sufficient. With the known connection between the resolution and event statistics (e.g., the number of collected events in the imaging session) there will be different implications as to the radiation dose necessary to produce good quality images. Most of other imaging cases will be most likely in-between these two extreme "small lesion" (high resolution) and "pattern" (spatial resolution) situations. Indeed, the present disclosure is focused on task-specific performance, and the results of system optimization, including the radiation dose, will depend, at least in part, on the particular case. At this end, the present disclosure connects with the individual medicine approach, as the optimal parameters will be disease- and organ-, but will also include patient-specific.

There is a whole range of diagnostic tests whose acceptance and availability (lower cost) will greatly benefit from lowering the injected radiation doses. Two such special diagnostic topic subjects are the screening for breast cancer, and the screening for Alzheimer's and other dementias. In the case of breast cancer, many women in the high risk groups who end up with inconclusive mammograms have no powerful adjunct screening technique to follow up with. While both MRI and US provide excellent structural results, there provide limited biological information.

The availability of low-dose screening test for Alzheimer's using dedicated high efficiency and low-cost PET brain imager combined with one of the recently developed and approved for human use PET imaging agents, could revolutionize the field of patient management for patients struck by this horrible disease. It offers hope that by enabling early diagnosis to many more patients, and the longitudinal studies with multiple low dose radiation injections, different paths for cure can be studied in a much faster time frame on a larger pool of patients. By this, the discovery and evaluations of the proper treatment for the millions of affected patients may be effectuated.

While the main focus of possible improvements discussed here is with respect to PET, the same general arguments can apply to SPECT imaging. The specific improvements in SPECT that can lead to lowering injected radiation doses include, but are not limited to:

Improvements in collimators and selection of optimal collimators for the task.
Increase in angular coverage.
Simultaneous multiple views, for example, double-sided imaging in breast images.
More specific imaging agents with higher diseased tissue/healthy tissue uptake ratios.
SPECT inserts in MRI with MRI providing the co-registered anatomic information, relaxing the demand for higher statistics in SPECT images.

The separate special subject theme is the imaging of pediatric patients, e.g., infants and small children. The current radiation doses, even when normalized to the child's body weight, are often deemed too risky and, therefore, a barrier against the even potentially life-saving diagnostic tests is raised. Lowering the radiation dose by, for example, a factor of around 10, would dramatically change the perception and the reality of the radiation exposure to children patients.

Another special situation concerns intra-operative imaging in surgery. This is a potentially very important niche area of implementation for dedicated compact mobile molecular imagers assisting with cancer margin definition in surgery, in order to assure full extraction of cancerous tissue (at the macroscopic level). There is a concern about the multiple and repetitive radiation doses received by medical personnel (e.g., surgeons, nurses and anesthesiologists) during surgeries involving injections of radiolabeled imaging agents before the patient goes to surgery. Establishing new standards, for example, for F18-FDG injections at a substantially lower level than 37 MBq (10 mCi) would greatly facilitate acceptance of such an imaging intraoperative procedure.

PET/MRI multimodal imaging is a major challenge to the imaging field. PET uses photomultiplier tubes for detection of scintillation light. Unfortunately, both imaging techniques detract from the operation of the other. For example, the magnetic field created by MRI scans impacts light yield of scintillator materials, thus causing interference in the PET imaging process. In addition, the PET detector causes disturbances to the magnetic field, leading to artifacts in the MR images.

Several approaches have been considered to overcome these issues, including creating a tandem system, complete integration, or a PET insert system. The tandem PET/MRI system would be similar to that of the PET/CT system where the patient is moved from the PET imaging field of view to the MRI field of view. (See e.g., Zang-Hee C, Young-Don S, Hang-Keun K, Kyoung-Nam K, Se-Hong O, Jae-Yong H, et al.: A hybrid PET-MRI: an integrated molecular-genetic imaging system with HRRT-PET and 7.0-T MRI, Int'l J. Imaging Sys. Tech. 2007; 17:252-65). Though relatively simple to implement, and with little barriers to entry in terms of development, FDA approval, etc., such a system is still not a true simultaneous PET/MRI scan and patient movement could cause a misread by either system. Current commercial tandem products of such a system include Phillip's INQENUITY TF™ system and GE's PET/CT+ MRI™ system.

A completely integrated system is desirous but also very challenging, as there are physical space limitations and major issues of interference. There are many groups that have created prototypes of various architectures in this space. (See e.g., Lucas A J, Hawkes R C, Ansorge R E, Williams G B, Nutt R E, Clark J C, et al.: Development of a combined microPET-MR system, Technol Cancer Res Treat 2006; 5:337-41; and Handler W, Chronik B, Scholl T, Gilbert K, Peng H.: Combining field-cycled magnetic resonance imaging with positron emission tomography (abstract), J Nucl Med Meeting Abstracts 2007; 48(Suppl 2):89P). However, most of these approaches are preclinical and in early stage. Recently, Siemens Healthcare developed a fully integrated hybrid PET/MRI and received FDA approval. However, there has been little traction in sales, due to such issues as expense of the machines, room size requirements for the machines, training for the machines, and lack of approved billing codes for the procedure.

An alternative to the tandem and the fully integrated systems identified above is the PET insert system of the present invention, where a removable PET scanner, designed to be MRI-compatible, is used within any MRI system. In the present disclosure, the inventors herein have created such a portable PET imager. In one embodiment, the portable PET imager is in the form of a ring of individual detection modules (currently fitted tightly around the patient's head; although later could be fitted to other anatomical regions). The technology used by the inventors herein includes, for example, a Silicon Photomultiplier ("SiPM") photo sensor. For maximum performance, it is contemplated that the PET inserts require installation of MRI-model specific RF coils that would minimize the interference between the MRI and the PET insert. However, the inventors herein contemplate imaging performed with either the whole body RF coils built into the MRI scanner or standard flexible coils delivered with the scanner. The overall approach contemplated herein is to have the PET inserts operate within any MRI scanner, with only minimal changes.

The inventive techniques described herein offer various advantages, some of which include:

A compact PET machine, which could stand-alone.

The ability to work with current MRI machines.

Cheaper than current MRI/PET scanners.

Inserts can be organ specific, eliminating full body scan.

The key guiding new paradigm philosophy behind the inventive concept is that it is possible, by implementing relatively technically simple and robust and economical means, to convert practically any MRI scanner to an organ-specific PET/MRI imager (e.g., brain, head/neck, breast, prostate, colon, gynecological, pancreas, stomach, extremities, etc.). The strong motivator for this concept is that while the new hybrid PET/MRI imagers have important advantages over standard PET/CT systems, they are very expensive, often up to 3-4 times the PET/CT scanner cost. It is also postulated herein that no, or only minimal, additional adaptation means are necessary through implementation of properly designed organ-specific PET inserts in MRI scanners to obtain good quality PET/MRI images of the selected organ or body part.

It is contemplated herein that the universal, MR scanner-independent portable PET inserts will not require any special attachment procedures to operate with MRI scanners. The only requirement will be to validate that the quality of the MRI images (e.g., signal-to-noise, uniformity, etc.) will not be impacted by the PET inserts. Therefore, the present inventive concept is an enabling concept to propagate the implementation of a life-saving PET/MRI diagnostic technique by offering a "kit" of PET inserts that can be used with any MRI scanner. At present there are an estimated 36,000 MRI scanners in the world.

In one form, the PET detector insert modules are placed very close to the patient body to make them more compact and mechanically compatible with operation inside the magnet bore of the MRI, and also to increase detection sensitivity. In the case of brain imaging, the detection modules form a tight ring allowing only for an insertion of the thin RF coil between the ring and the patient's head The universal portable PET inserts of the present invention which are placed inside the bore of an MRI scanner have no active electronics on-board, except the photodetectors (e.g., Silicon Photomultipliers or Avalanche Photodiodes). The active electronics, in this case, are at a convenient distance outside the magnet bore, typically 1-10 feet counting from the edge of the bore.

In an alternate form, the PET insert component is placed outside the inner standard solid or flexible RF coil, while both the insert and the RF coil are placed inside the bore of the MRI scanner. The PET insert has no active electronics on-board, except the photodetectors (e.g., Silicon Photomultipliers or Avalanche Photodiodes). In this case, some of the active electronics (such as, for example, front-end amplifiers) can be still in the magnet bore, although they should be at a convenient distance from the end of the RF coil, typically 1-20 inches.

In another form, specialized PET inserts on-board passive readout electronics (comprised only of resistors, capacitors and diodes) is analog position-encoding. This substantially reduces the number of readout analog signals that need to be sent to the electronic circuitry placed outside the magnet bore, and then sent to the digitizing circuitry. Additionally, this substantially reduces the complexity and cost of the PET inserts themselves.

As contemplated herein, there need be no special RF coil incorporated or integrated with the PET inserts. For example, in a further form, it is contemplated that the only RF coils used during the combined MRI and PET imaging sessions are: (1) the standard whole body coil; or (2) the manufacturer provided standard solid or flexible attachment coil(s). This reduces the cost and complexity of the PET inserts.

The calibration and the uniformity correction of the tomographic reconstruction response of the inventive imager are typically performed by simulations, but also can be done experimentally by implementing uniform phantoms. In the case of a ring imager, a cylindrical uniform phantom is placed inside the ring and the high statistics reconstructed images are used as the base of the system response. In this way, geometrical response non-uniformities, which are ever present in any system, are recorded and appropriate correction measures can be undertaken. For example, the reconstructed object or patient images can be divided by corresponding uniform phantom images. This very simple technique offers immediate "on-the-go" uniformity, and also absorption correction. However, more sophisticated correction techniques can also be used involving, for example, a mixture of simulation and experimental data.

Figure 2:
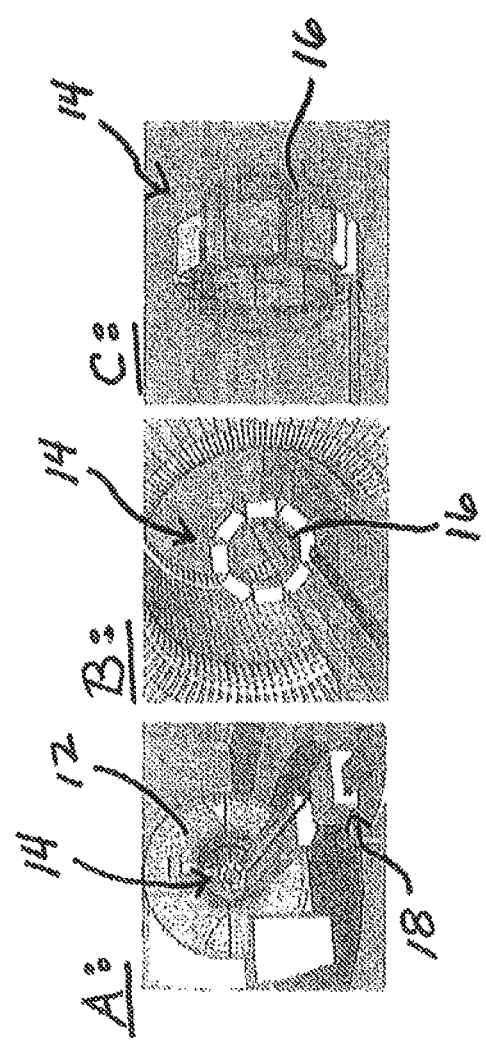
FIGS. 2A-C illustrate various views of the PET insert of the present invention provided within an MRI scanner.
Figure 3:
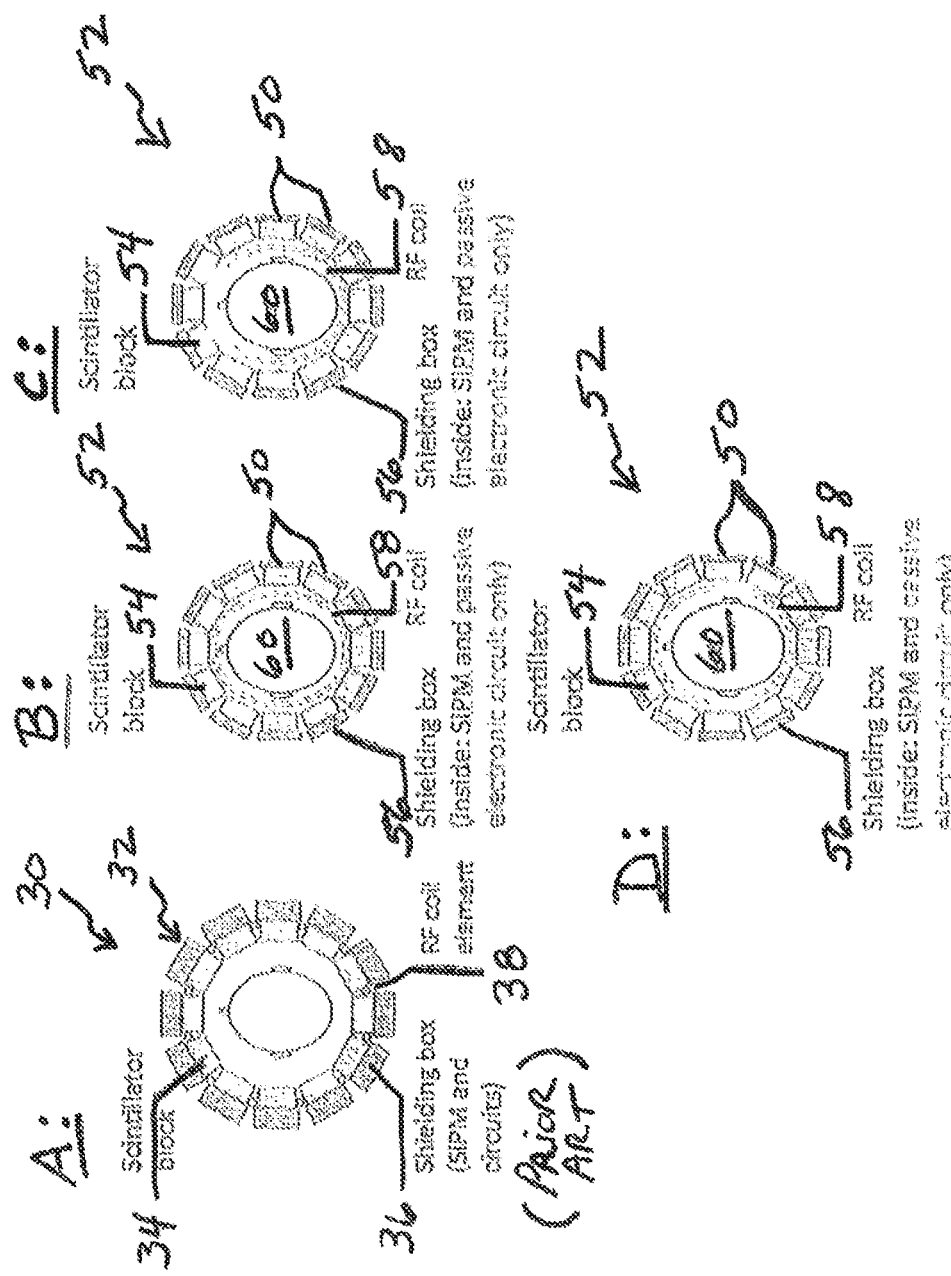
FIGS. 3A-D illustrate conceptual views from above the patient's head of the PET inserts of the present invention configured as a brain imaging system including a ring of detector modules arranged around the patient's head (FIG. 3A illustrates a prior art device)

FIGS. 1-2 illustrate one implementation form of the PET insert of the present invention configured as a brain ring. FIG. 1 illustrates an MRI scanning room, shown generally at 10. The room 10 includes an MRI scanning device 12. A PET insert 14, in the form of a brain ring, is provided which is designed to fit around the head of a patient and be received within the magnetic bore of the MRI scanner 12 while being worn by the patient. The PET insert 14 also includes an RF coil 16, shown more clearly in FIGS. 2-3. Only the basic necessary front-end PET ring electronics 18 (shown in FIG. 1 on a small MR-compatible cart) stay inside the MRI room 10, and the remaining processing electronics, data acquisition system (DAQ) and computer with DAQ- and processing-software, shown at 20, are placed in a wheeled cabinet/rack outside the MRI room 10, and preferably in the MRI operator room. A screened cable bunch 22 connects the electronics 18 inside the MRI room 10 with the rack/cabinet electronics 20 outside the MRI room 10, exiting the MRI room 10 via a provided standard wall port 24. The RF coil 16 is placed inside the ring of PET inserts 14 and preferentially extends past the edge of the PET insert 14 (as shown in FIG. 2C).

FIGS. 3A-D illustrate conceptual views from above the patient's head of the PET inserts of the present invention configured as a brain imaging system including a ring of detector modules arranged around the patient's head (FIG. 3A illustrates a prior art device).

FIG. 3A illustrates a prior art brain imaging system 30, which includes a set of photodetector modules 32 formed as a ring for fitting around the head of a patient. (See e.g., F. Nishikido, et al.: *Feasibility study for a PET detector integrated with an RF coil for PET-MRI*, presented at and in the conference record of the 2011 IEEE Medical Imaging Conference, 23-29 Oct. 2011, Valencia, Spain). The photodetector modules 32 each include respective scintillator blocks 34 and shielding boxes 36. As shown in FIG. 3A, an RF coil 38 is integrally built into the PET ring 30. Additionally, the shielding boxes 32 each includes SiPM photo sensors and active electronic circuitry. This enables the ring 30 to operate as a stand-alone brain scanner.

FIGS. 3B-D illustrate the novel PET inserts 50 (i.e., detector modules) formed as a ring 52 designed to fit around a patients head. Each of the detector modules 50 includes respective scintillator blocks 54 and shielding boxes 56. Of important note is that the shielding boxes 56 include no active circuitry (they include passive electronic circuitry only), except for SiPM light sensors. Additionally, an RF coil 58 placed between the object to image (e.g., patient's head 60) and the ring detector modules 50. In case of PET ring 52, as shown herein, the RF coil 58 is placed close to the inner ring surface. Additionally, the coil 58 does not have to cover the full angular range, but can offer only partial coverage. Further, the coil 58 could be also made of several pieces-sectors in lieu of the one contiguous element. For example, FIG. 3B shows a coil 58 extending around the entire angular displacement; FIG. 3C shows the coil 58 extending only partially around the angular displacement; and FIG. 3D shows a coil 58 having a two-piece, front-back configuration. As contemplated herein, a preferred coil type is one of the flexible standard coils from the package of coil attachments to the particular MRI scanner model. Such coils are typically provided with the MRI scanner module. Further, while FIGS. 3B-D show twelve detector modules 50 forming the ring 52, any number of detector modules 50 may be used without departing from the spirit and scope of the present invention.

FIGS. 4A-C depict a prior art system incorporating a brain PET/MRI insert concept. Such a system is described particularly at:

- K. J. Hong, Y. Choi, J. Kang, W. Hu, J. H. Jung, B. J. Min, Y. H. Chung, and C. Jackson: Performance evaluation of a PET detector consists of a LYSO array coupled to a 4×4 array of large-size GAPD for MR compatible imaging, J. Instrum., vol. 6, P05012, 2011.
- J. Kang, Y. Choi, K. J. Hong, J. H. Jung, W. Hu, Y. S. Huh, H. K. Lim, and B-T Kim: A feasibility study of photosensor charge signal transmission to preamplifier using long cable for development of hybrid PET-MRI, Med. Phys., vol. 37, pp. 5655-5664, 2010.
- J. H. Jung, Y. Choi, K. J. Hong, W. Hu, J. Kang, B. J. Min, S. H. Shin, H. K. Lim, Y. S. Huh, and E. J. Kim: *Development of a position decoder circuit for PET consisting of GAPD arrays*, Nucl. Instr. and Meth., vol. A 621, pp. 310-315, 2010.
- W. Hu, Y. Choi, K. J. Hong, J. Kang, J. H. Jung, Y. S. Huh, H. K. Lim, S. S. Kim, and B. T. Kim: *A simple and improved digital timing method for positron emission tomography*, Nucl. Instr. and Meth., vol. A 622, pp. 219-224, 2010.

However, problems with this prior art approach are that, as shown in FIG. 4B, a specially built RF coil 80 must accompany the PET ring, and include a PET gantry 82, a PET gantry holder 84 and an RF coil holder 86. These items add to the complexity, cost and size of the device. Additionally, the prior art design has to have an additional stand-off distance between the PET ring and the object (head in this case) and larger ring diameter to accommodate the applied RF coil(s) 80. By this, the prior art system loses flexibility and portability. The complexity and cost also increases. In addition, the detection sensitivity of the ring is lower for larger diameters of the ring, resulting in a degradation of performance.

Figure 4:
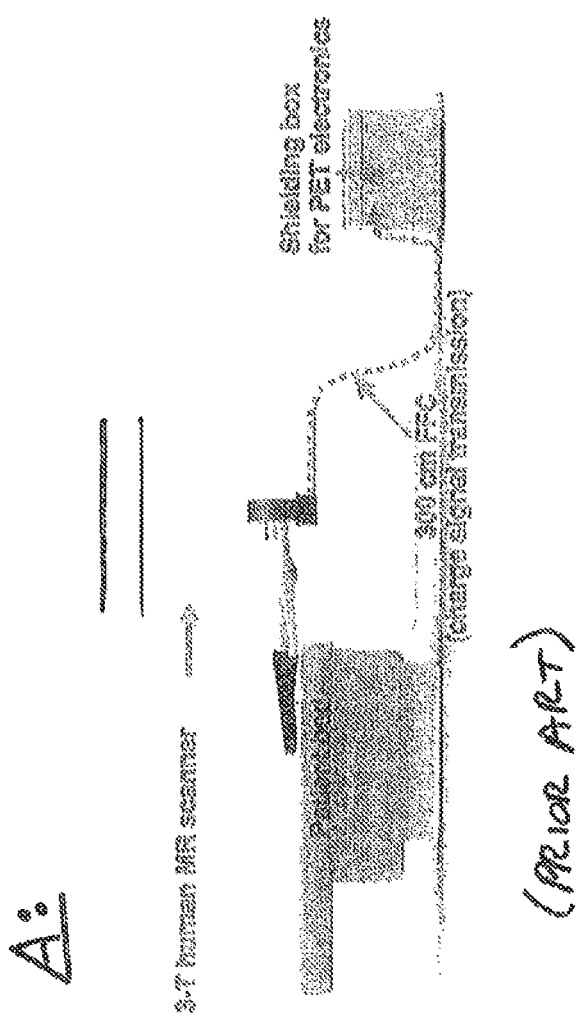
FIGS. 4A-B illustrate a prior art PET/MRI system.
FIG. 4C is a data flow diagram of the prior art PET/MRI system of FIGS. 4A-B.
Figure 4:
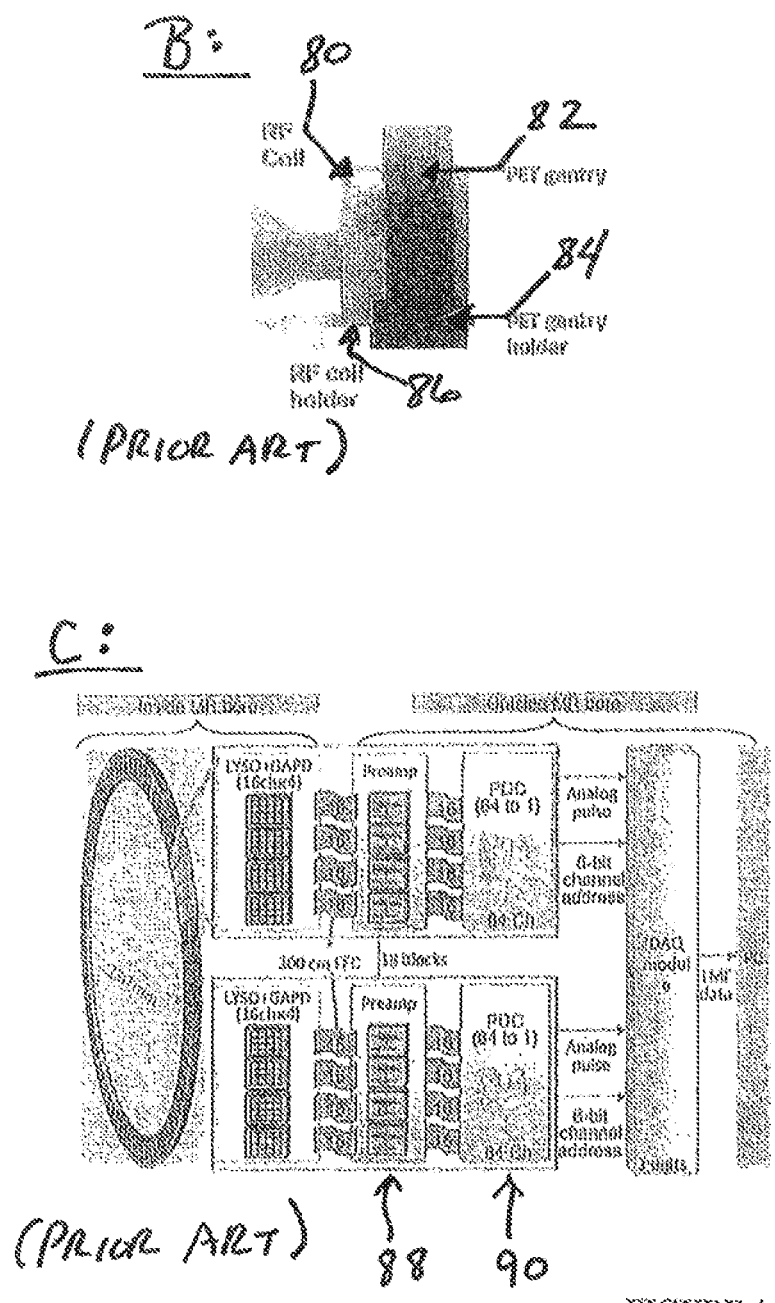

In contrast, the inventive concept disclosed herein includes a PET ring design that very closely follows the patient's head. Additionally, the present invention does not use a specially built RF coil accompanying the PET ring, nor the standard brain coil. In contrast, the present invention, in a preferred embodiment, uses a standard flexible RF coil provided with the MRI scanner, allowing for much tighter structure of the PET ring. While both the present invention and the prior art device shown in FIG. 4 place the electronics box outside the magnet bore of the MRI scanner, the present invention utilizes an on-board analog readout that is position-encoded with highly reduced number of exiting analog signal channels. Such position encoding is not found in prior art devices. For example, as shown in FIG. 4C, analog signals from all SiPM channels (a separate signal channel is required for thousands of 3 mm SiPM pixels) have to be sent to the pre-amplifying electronics, shown at 88, and then only after compression in a position decoder 90, are the analog signals sent to digitizing electronics. This results in a more complicated, bulky and expensive readout system.

Two readout systems with minimal electronic circuitry on board the PET inserts are important to the overall concept of the present invention, as described below.

In a basic variant, each of the SiPM modules (built out of an array of N×M individual SiPM pixels) has a passive (e.g., made out of resistors, capacitors, diodes) charge division circuit that reduces the number of analog channels from N×M to four. In the basic variant, only these four channels per module are exiting the PET insert in the MRI magnet bore and connect via the cable to the processing circuitry In a higher performing variant, the analog outputs from the N×M array of SiPM pixels are reduced in the passive charge division circuit to N+M sector analog outputs. These N+M module outputs can be further connected, or chained, to form panel/sector "super-modules" in order to reduce the number of sector readout channels.

FIGS. 5-6 illustrate the general concept of how to implement the high performing channel-reducing on-board (the PET insert) passive circuitry (using only resistors, diodes and capacitors), where the row and column outputs from individual detector modules, that are arranged in rings or panels, are passively chained to form X and Y readout sectors. For example, FIG. 5 shows a 4×2 module panel in a two-ring PET insert; and FIG. 6 shows a 4×3 module panel in a three-ring PET insert. Such an 8-module group could be a 4×2 module panel (as shown in FIG. 5), but also a sector in a two-ring PET insert, etc. In this example of an 8-module panel, each 144 SiPM pixels of SensL model ArraySL-4P9 is reduced to 12 X+12 Y sectors, and for the whole panel the numbers are: 48 X+24 Y=72 channels. This needs to be compared with a direct readout of all SiPM pixels in this panel, which is equal to 144×8=1152. A channel reduction factor of 16 is thus achieved in this example. A similar channel reduction following a similar approach can also be achieved for the 4×3 module panel shown in FIG. 6. In marked contrast, prior art approaches require signals from all SiPM pixels to be first exited from the magnet bore and amplified, before they would be processed in any channel reducing circuitry, resulting in increased complexity, cost and space requirements.

Figures 7, 8:
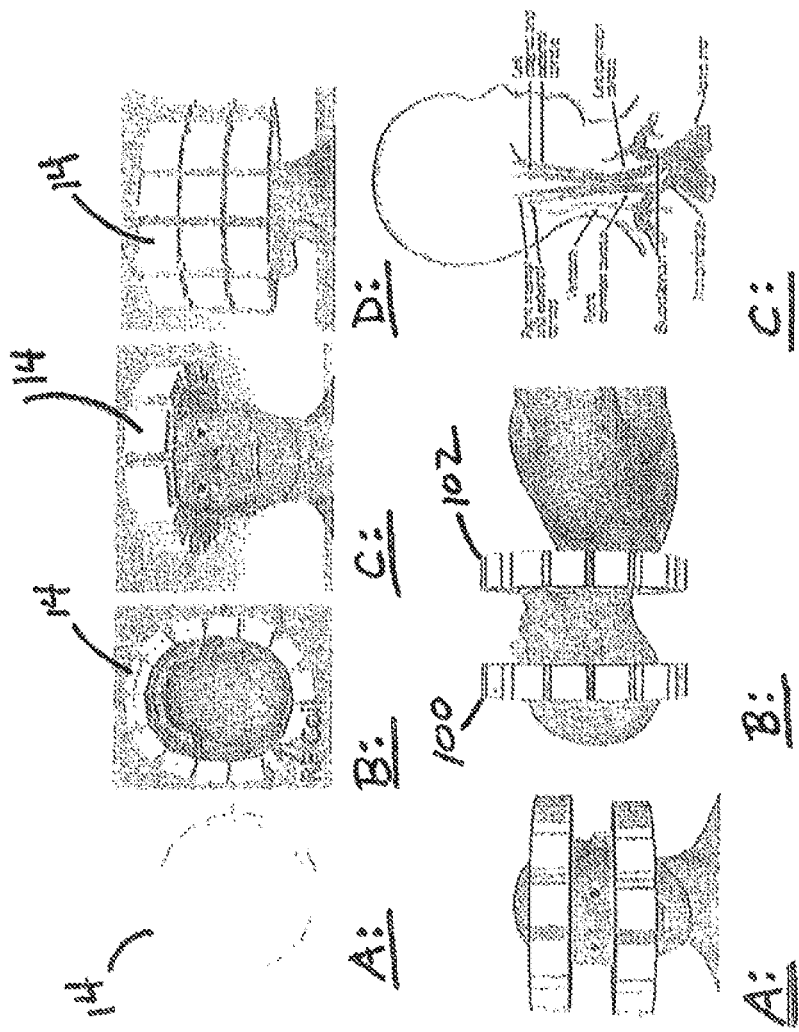
FIGS. 7A-D illustrate exemplary single and multiple PET rings for imaging the head of a patient.
FIGS. 8A-C illustrate exemplary multi-ring, spaced apart PET imager for imaging the head and/or neck regions of a patient.

The present invention may take a variety of forms to suit a variety of different applications. For example, FIG. 7A illustrates an example of a schematic of a single imager PET ring, shown herein with twelve individual MRI-compatible PET modules 14, which are divided into two parts, for easy placement and adjustment on, for example, the patient's head/brain/neck. Each of the individual modules 14 is made from a matrix of pixelated LYSO crystals coupled to an array of solid-state Silicon Photo-Multipliers (SiPM). FIGS. 7B-C illustrate an example of an elongated PET ring built with fourteen individual modules 14, which is better adapted to the shape of the human head. As will be appreciated, any number of individual modules 14 may be incorporate into a given design without departing from the spirit and scope of the present invention. In a simplest variant, only a single ring of modules 14 is built. However, multi-ring systems, such as, for example, the three-ring system shown in FIG. 7D, that will cover the whole brain in one position can be built.

Additionally, in further exemplary embodiments, the rings need not be spaces adjacent one another. FIG. 8A illustrates such a two-ring variant with two rings spaced apart with an adjustable spacing. Such an "open PET" type arrangement provides a larger field of view at a reduced complexity and cost. In a particular special case, as shown in FIG. 8B, one of the rings 100 can be place above the ears at the brain level, while another ring 102 can be placed at the neck level, for example, during first path dynamic blood flow imaging with the neck ring measuring the so called input function in the carotid artery, as shown in FIG. 8C. The MRI RF coils—not shown here—are placed inside all of the rings. It will be appreciated by one skilled in the art that multiple rings and various spacing may be utilized.

Figure 9:
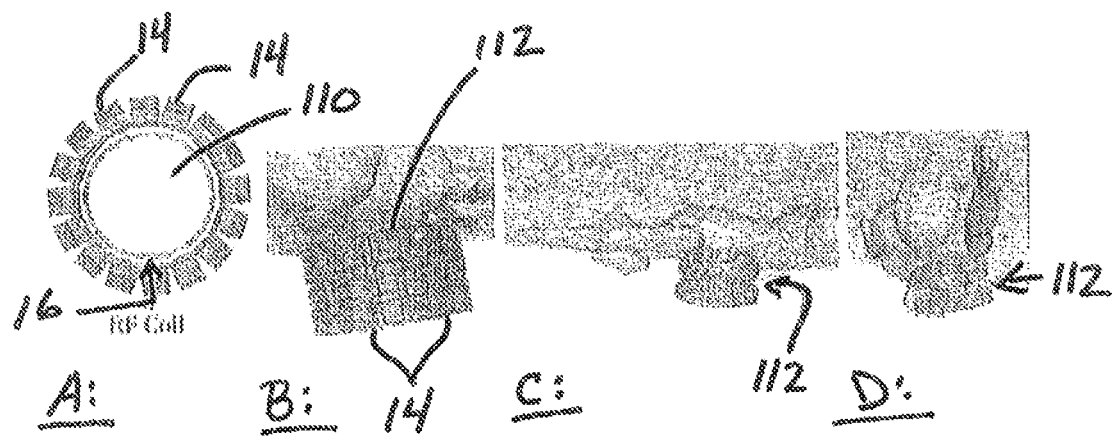
FIGS. 9A-D illustrate an exemplary embodiment of the present invention utilized for breast scanning with the patient in a prone position.

FIGS. 9A-D illustrate an embodiment of the present invention utilized for breast scanning with the patient in a prone position. FIG. 9A illustrates the PET modules 14 formed as a ring for receiving a breast 110 of a patient. The RF coil 16 is provided between the modules 14 and the patient's breast 110. While not shown in FIG. 9, the RF MRI coils are provided between the breast 110 and each of the rings of PET modules 14. The PET breast inserts can also have single (FIG. 9A), two (FIGS. 9C-D) or three (FIG. 9B) or more rings. In a multi-ring variant, the top ring will typically be placed adjacent the chest wall. It is important in this case that the imager's active edge extends to the chest wall so that the PET coincidence lines of response ("LORs") at the upper edge of the imager (shown as dashed line 112) include the tissue at the base of the breast 110. The number of rings can vary depending on the size of the patient's breast. In the two-ring Open PET variant, the top ring is typically placed by the chest wall. The patient typically will be placed prone in the MRI scanner in this variant. Position of the rings can be adjusted up and down. As shown in FIGS. 9C-D, a gap 112 is provided between the rings in the Open PET variant. This gap 112 may be adjustable from down to almost zero to more than the width of each of the rings (for example, to enable lesion biopsy).

Figure 10:
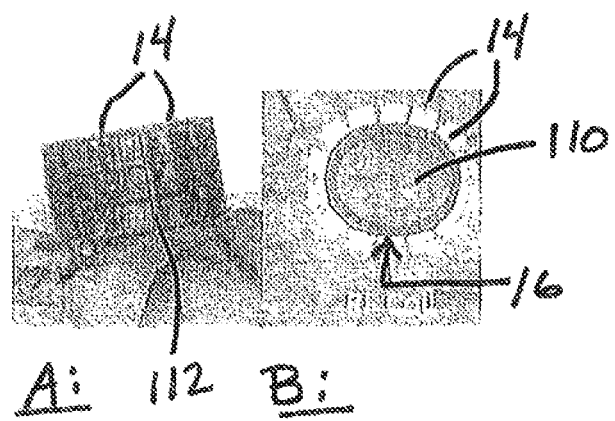
FIGS. 10A-B illustrate an exemplary embodiment of the present invention utilized for breast scanning with the patient in a supine position.

FIGS. 10A-B illustrate an embodiment of the present invention utilized for breast scanning with the patient in a supine position. FIGS. 10A-B illustrates the PET modules 14 formed as a ring for receiving a breast 110 of a patient. The RF coil 16 is provided between the modules 14 and the patient's breast 110. While not shown in FIG. 10, the RF MRI coils are provided between the breast 110 and each of the rings of PET modules 14. The ring(s) can extend vertically from a couple of cm to 10 cm or even more, balancing the width of the breast slice seen in one shot against the cost and complexity. It is important in this case that the imager's active edge extends to the chest wall so that the PET coincidence lines of response ("LORs") at the lower edge of the imager (shown as dashed line 112) include the tissue at the base of the breast 110. Positioning of the 1-3 ring (or more) cylinder with proper angling will be key in achieving this goal. An oval ring shape may also be considered to allow for even better positioning than the circularly shaped ring. As with other embodiments, matching flexible RF coil(s) 16 will be placed inside the ring(s).

FIGS. 11A-E illustrate an embodiment of the present invention utilized for prostate imaging. In one form, as shown in FIGS. 11A-E, the PET inserts 14 are formed as PET panels 120. In one form, the panels 120 can be composed of twelve individual modules 14, for example, a 3×4 array, with each module 14 being approximately 5 cm×5 cm in size. However, other numbers of modules, arrays and sizes of panels 120 and modules 14 may be implemented without departing from the spirit and scope of the present invention.

Figure 11:
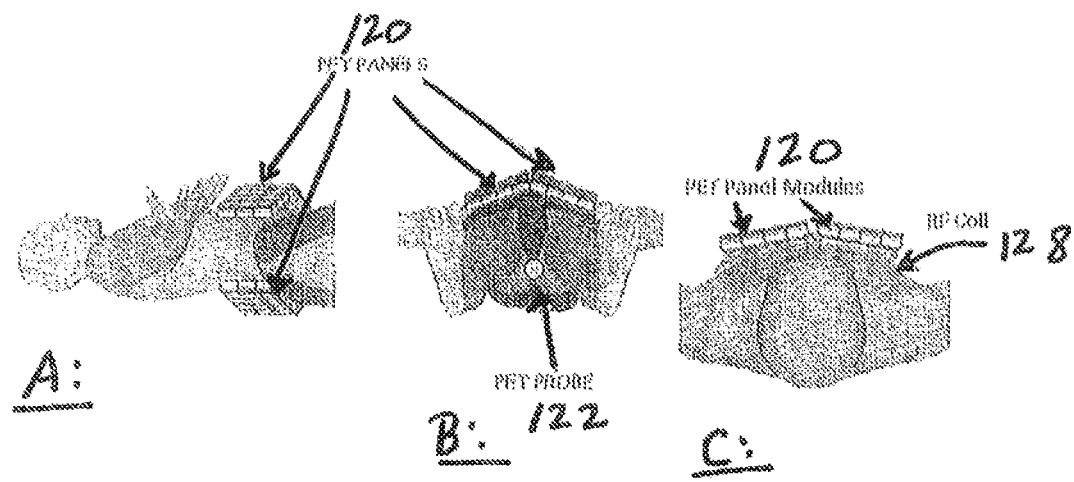
FIGS. 11A-E illustrate an exemplary embodiment of the present invention utilized for prostate imaging.
Figure 11:
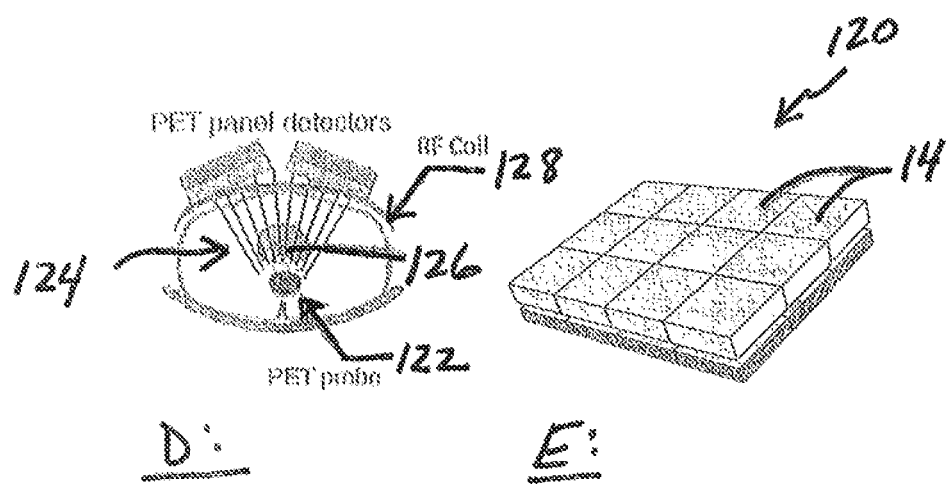

As shown in FIG. 11A, in one exemplary embodiment for prostate screening, four individual high resolution panel detectors 120 may be implemented, with two on the upper portion of the patient body and two on the lower portion. In an alternate embodiment, as shown in FIGS. 11B and D, an endorectal sub-mm PET probe 122 my being inserted in the patient's anus and operates in coincidence with the two top PET panel modules 120. FIG. 11D shows the response signals 124 that are generated between the panels 120 and probe 122 and through the prostate gland 126. While RF coils 128 are pictured in FIGS. 11C-D, it will be understood that RF coils 128 are implemented in each embodiment shown in FIG. 11 and disposed between the PET panel detectors 120 and the patient's body.

Figure 12:
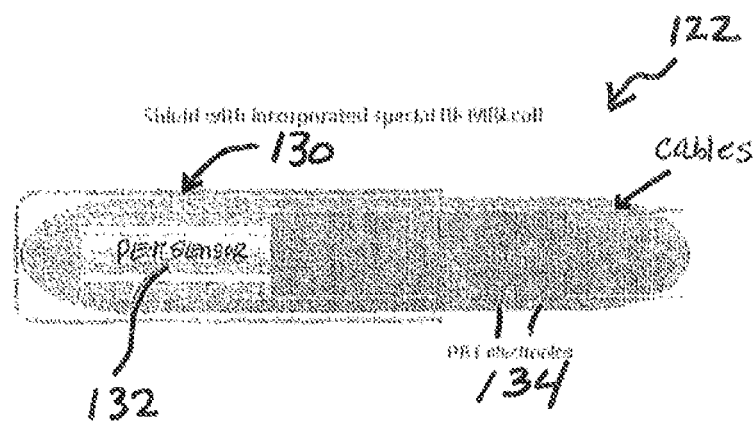
FIG. 12 illustrates an exemplary endorectal PET probe utilized for prostate screening.

FIG. 12 illustrates an exemplary endorectal PET probe 122 utilized for prostate screening. The probe 122 is inserted in the external, generally cylindrical tube 130, which provides mechanical means to stabilize the prostate during the PET/MRI scans. The tube 130 also incorporates also a special RF coil (not shown) to limit the interference of the PET sensor 132 (i.e., probe element) with the on-board input stage electronics 134 on MRI operation. Cables 136 connect the PET sensor 132 and the PET electronics 134 to the electronics remote from the MRI device. In principle, the overall system (see FIGS. 11-12) may be operated in a simultaneous PET/MRI mode. Alternatively, the PET probe 122 may be removed during MRI imaging (leaving the external tube 130 with the coil inside the patient), to minimize interference of the PET insert 122 with the MRI operation, therefore resulting in a sequential PET/MRI imaging. The external PET panel modules 120 (see FIG. 11) will stay in place during the MRI scans.

Figure 13:
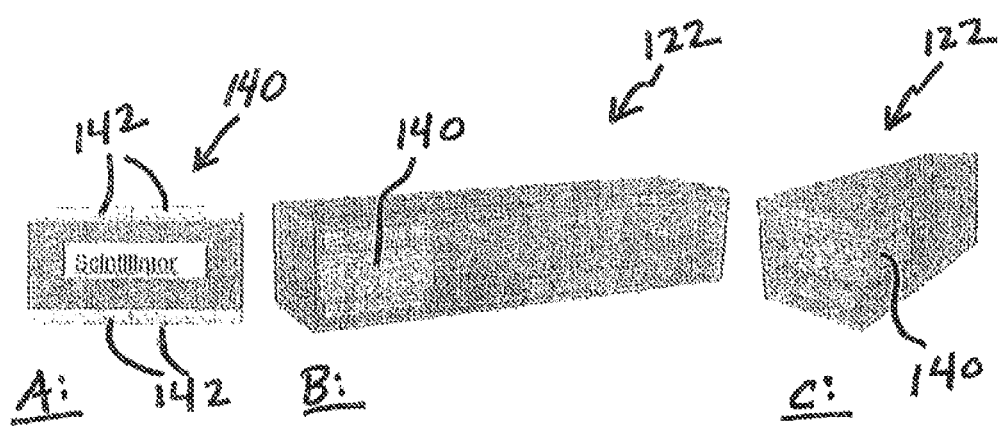
FIGS. 13A-C illustrate conceptual diagrams of the exemplary endorectal PET probe sensor shown in FIG. 12.

FIGS. 13A-C illustrate conceptual diagrams of the endorectal PET probe sensor 122 based on a double-sided readout of the scintillation array, shown at 140. The scintillator array 140 generally includes two top and bottom SiPM arrays, shown at 142. The containment tube 130 (see FIG. 12) is shaped to have minimal cross-section (e.g., less than 35 mm in size). The same probe 122 could be also used intra-vaginally in the detection of selected gynecological cancers.

Figure 14:
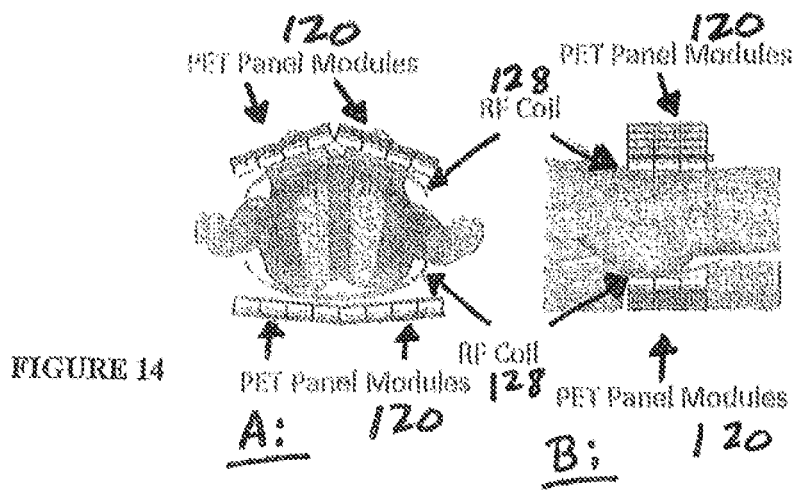
FIGS. 14A-B illustrate an exemplary embodiment of the present invention utilized for vaginal imaging.

FIGS. 14A-B illustrate an exemplary embodiment of the present invention utilized for vaginal imaging. FIGS. 14A-B shows PET panel modules 120 provided on the upper and lower portions of a patient to surround the patient in the vicinity of the pelvic region for vaginal screening. In this example, the PET panels 120 include four panel detectors (two on the top and two on the bottom), with each panel 120 built, in this example, with 12 individual MRI-compatible PET modules 14, approximately 5 cm×5 cm in size (preferably in a 3×4 array). However, other numbers of modules, arrays and sizes of panels 120 and modules 14 may be implemented without departing from the spirit and scope of the present invention. The system is divided into two sectors—top and bottom—each with two panel detectors 120, for easy placement and adjustment around the patient inside the MRI scanner. The bottom panels 120 will need to be incorporated in the raised support for the patient. Each of the individual modules 14 is preferably made from a matrix of pixelated LYSO crystals coupled to an array of solid state Silicon Photo-Multipliers ("SiPMs"). RF coils 128 are provided between the PET panels 120 and the patient's body. The PET probe 122 is not shown in FIG. 14. However, similar to the prostate case, there are there are two possible variants of the PET probe 122 implementation intra-vaginally, or endorectally, one with and one without.

Figure 15:
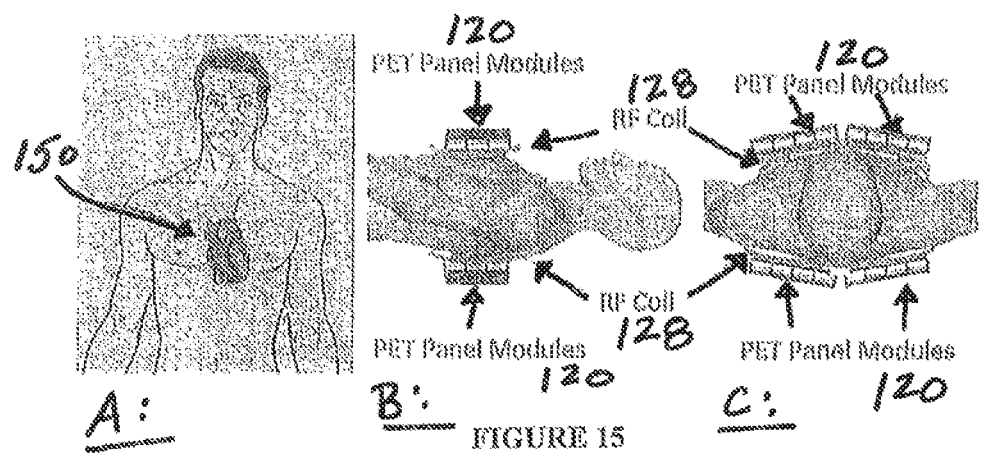
FIGS. 15A-C illustrate an exemplary embodiment of the present invention utilized for cardiac imaging.

FIGS. 15A-C illustrate an exemplary embodiment of the present invention utilized for cardiac imaging of the heart 150 and surrounding region. In this embodiment, similar to the embodiment shown in FIG. 14, four imaging PET panels 120 are inserted in the MRI scanner to provide good angular coverage of the region of the heart. The PET panel modules 120 are provided on the upper and lower portions of a patient to surround the patient in the vicinity of the chest region for cardiac screening. In this example, the PET panels 120 include four panel detectors (two on the top and two on the bottom), with each panel 120 built, in this example, with 12 individual MRI-compatible PET modules 14, approximately 5 cm×5 cm in size (preferably in a 3×4 array). However, other numbers of modules, arrays and sizes of panels 120 and modules 14 may be implemented without departing from the spirit and scope of the present invention. The system is divided into two sectors—top and bottom—each with two panel detectors 120, for easy placement and adjustment around the patient inside the MRI scanner. The bottom panels 120 will need to be incorporated in the raised support for the patient. Each of the individual modules 14 is preferably made from a matrix of pixelated LYSO crystals coupled to an array of solid state Silicon Photo-Multipliers ("SiPMs"). RF coils 128 are provided between the PET panels 120 and the patient's body.

Figure 16:
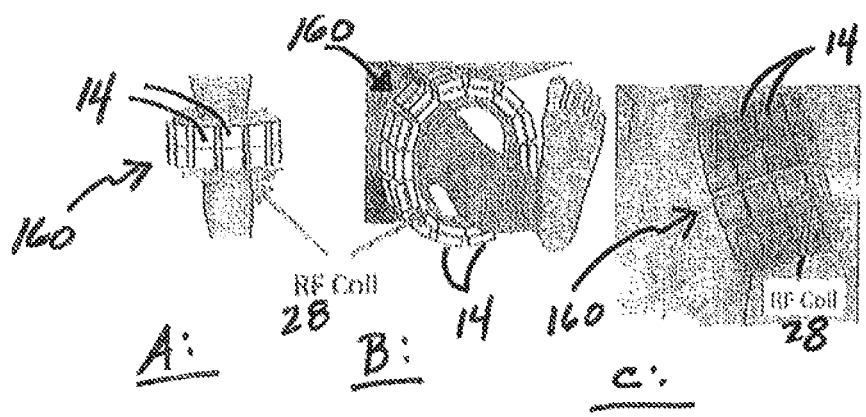
FIGS. 16A-C illustrate exemplary embodiments of the present invention utilized for extremity (arm and leg) imaging.

FIGS. 16A-C illustrate exemplary embodiments of the present invention utilized for extremity (arm and leg) imaging. FIGS. 16A-B shows the PET modules 14 formed as a ring 160 and used for scanning a patient's leg, for example, around the knee area. FIG. 16C shows the PET modules 14 formed as a ring 160 and used for scanning a patient's arm, for example, around the shoulder area (for example looking for involved lymphatic nodes in case of breast cancer). Of course, other areas of the arms and legs, as well as other extremities, are contemplated. Multiple ring configurations may be employed (e.g., FIGS. 16A-B illustrate a two-ring configuration, while FIG. 16C illustrates a three-ring configuration), depending on the desired area to be imaged. As with other embodiments, the RF coil 28 is provided between the PET modules 14 and the patient's body.

The general inventive approach described herein minimizes any special requirements from the MRI scanner side prior to PET/MRI imaging. In principle, any MRI scanner can be turned into a dedicated organ-specific (e.g., brain, breast, head/neck, extremities, prostate, OB/GYN, etc.) PET/MRI hybrid imager with no or minimal adaptation. As no physical interaction through direct cable connection, etc. takes place between the PET insert and the MRI scanner, the approval procedure is highly simplified (no modification to MRI scanner is performed) and only limited cooperation from the MRI manufacturer is required.

This is in contrast with the common approach and prior art, as the assumption is generally made that one must use special coils, often incorporated in the PET inserts themselves. This requires that the add-on special coil be added through a special arrangement with an MRI scanner manufacturer. Adding the special coil physically to the set of coils requires recertification of the MRI scanner in each case for each MRI scanner model. These special integrated RF coils need to be individualized for each scanner type. This procedure adds complexity to the whole process, and requires strong interest and willingness on the side of the MRI manufacturer to cooperate. The present invention overcomes these drawbacks.

Assembly of the PET modules and configuration into rings, panels, etc. is within the technical knowledge of one of ordinary skill in the art. However, a few observations with respect to preferred embodiments will be noted. For example, in the assembly of one, approximately 5 cm square compact module of the first helmet PET prototype, four Hamamatsu SiPM arrays were assembled in a tight 2×2 array on one resistive readout base from AiT Instruments, Newport News, Va. Four 1.5 mm step 10 mm thick LYSO arrays from Proteus were coupled to form one compact scintillation module. There are no amplifiers or other active components (except the SiPM photodetectors) on board the detector module. They are in the distant electronics board (at the other end of the approximately 12 ft cable). There are 4 detector modules per one amplifier board.

The PET panels are composed of approximately 2"×2" modules, with 5 cm×5 cm SiPM photo sensors coupled to 50 cm×50 cm×10 mm LYSO scintillator arrays. These modules can be for, example arranged in 4×3 module panels. There are no electronics on board of the modules, except for the SiPM photo sensors. The SiPMs and passive readout circuitry (resistor and diode arrays) on board the modules are MRI compatible. The amplifier boards are located approximately 12 ft away outside the MRI bore, and are followed by, for example, the 64 ch DAQ box placed outside the MRI room, that is connected to computer via, for example, a USB2 link.

An assembled and lightproof compact PET ring can be made out of, for example, twelve detector modules, composed of LYSO arrays and MPPC arrays. Such rings were prepared for studies in the 3 Tesla MRI. Long cables connect between the twelve modules and a set of three 4 ch electronics boards for twelve detector modules, which are disposed outside of the MRI bore.

Construction of a prototype of the endorectal PET probe, as per the concept described above, can be effectuated, for example, using two 2"×2" arrays of the Hamamatsu monolithic MPPC modules (SIMPs). The LYSO array of 24×24 pixels of 1 mm×1 mm×10 mm pixels (1 mm pitch) is coupled at both sides to SiPM arrays. This array from Proteus is optimized for the Depth of Interaction ("DOI") double-sided operation. Teflon tape can cover a tight package with 8 monolithic MPPC modules and LYSO scintillation array having, for example, eight 20 cm long flexible flat cables with four of them bent by 180-degrees, to form a set of eight cables exiting outside of the probe and thus the patient. In this case, the amplifier boards will be attached to the ends of the cables, outside of the probe and the patient, thus minimizing the electronics' interference with the RF coil and the MRI.

FIGS. 17A-C illustrate brain images taken from a brain phantom using an exemplary ring embodiment of the present invention, demonstrating the PET operation of the PET ring. Summed reconstructed images from a set of ten 1 mm slices from a multi-layer multi-compartmental brain phantom (see FIG. 17B) filled with 450 microCurie F18 activity were taken. FIG. 17A illustrates a brain image a 30 minute run. FIG. 17C illustrates a brain image a 30 second run. The short run image (FIG. 17C) showed basically the same overall distribution pattern as the long image run (FIG. 17A), thus illustrating proper operation of the device.

Figure 17:
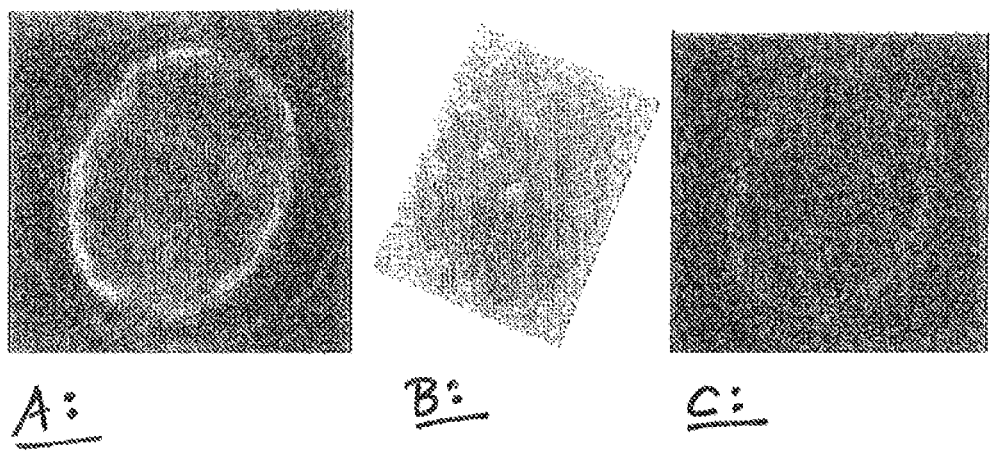
FIGS. 17A-C illustrate brain images taken from a brain phantom using an exemplary PET ring embodiment of the present invention.
Figure 18:
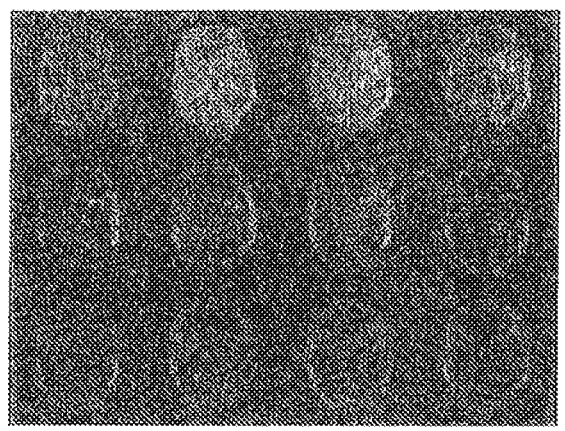
FIG. 18 illustrates twelve reconstructed 1 mm slices of the brain phantom obtained with an exemplary PET ring embodiment of the present invention.

FIG. 18 illustrates twelve reconstructed 1 mm slices of the brain phantom obtained with the PET ring, further confirming proper PET imaging operation of the ring PET device. In the examples of FIGS. 17-18, a brain phantom and a cylindrical "flood" phantom were used during measurements. The diameter of the active volume of the cylinder phantom was approximately 175 mm by about 50 mm in height.

Figure 19:
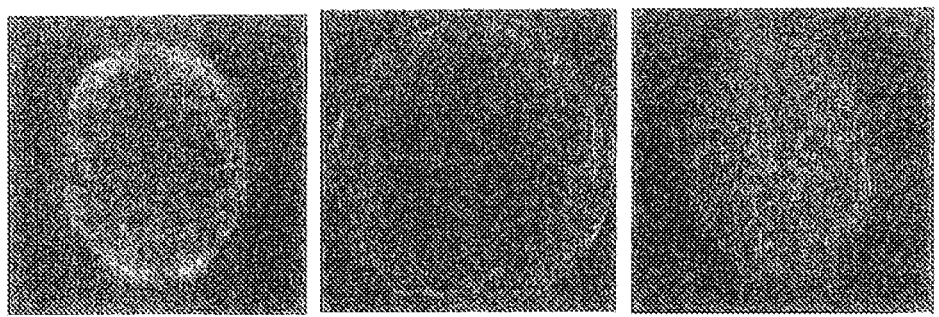
FIGS. 19A-C illustrate brain images demonstrating basic flood correction of the reconstructed images from an exemplary ring PET, in accordance with the present inventive.

FIGS. 19A-C are brain images demonstrating the basic flood correction of the reconstructed images from the ring PET, as per the present inventive concept. The single vertical slice of the reconstructed brain phantom shows serious non-uniformities before the correction (see FIG. 19A) using the image of the same vertical slice obtained with the uniformly filled cylinder phantom with water solution of radioactive-F18 (see FIG. 19B). The image shown in FIG. 19C shows that practically all artifacts were corrected for.

In accordance with an image correction procedure in accordance with the present invention, the first-order correction is performed by image division (using, for example, ImageJ software) of the (uncorrected) image slices obtained for the imaged object (such as, for example, phantom, or the patient's head, breast, extremity, etc.) by the corresponding slice images of the flood phantom. The flood phantom slice images can be pre-processed before the image division takes place, for example by smoothing or filtering with an optimally selected filtering function, to limit the effect of statistical fluctuations in the flood images on the final images obtained as the result of this division. Finally, filtering may be also performed on the normalized images, i.e., the results of the image division.

This uniformity correction not only accounts for the geometrical response matrix of the detector modules, but also for the bulk of the 511 keV annihilation gamma absorption effects. The geometrical response matrix includes the detector module response due to the fact that the detector ring is "broken" into modules/pieces with gaps between the modules. In addition, it corrects for the imperfections in the detector modules or the errors or in the calibration procedure. The latter effects can be seen as asymmetrical artifacts or non-uniformities in the detector module response. Also, at the edges of the imager's field of view, far from the center and approaching radially the detector modules, the effects of the depth of interaction ("DOI") (typically not corrected for in a simplified detector design) introduce additional non-uniformities. Series of flood images obtained for several diameter cylinders are stored in the image processing computer. Depending on the size of the imaged objects (e.g., head, brain, extremity, etc.) a different flood with best-matched size to the imaged object is used for the above correction procedure, as will be understood by one skilled in the art.

An example system of the novel inventive concepts described herein was assembled and tested. A twelve module PET ring was built according to the principles described herein of having no active electronics on board, and was inserted in the bore of the 3 Tesla Siemens MRI scanner. The electronics were placed in two locations: (1) amplifiers and power supplies (including the bias voltages for the operation of the SiPM based modules) were at the far ends of approximately 12 ft cables connecting at the input ends the detector modules, and placed outside the bore of the MRI scanner, close to the end of the patient table; and (2) in the electronics rack placed outside the MRI room having a data acquisition system ("DAQ"), a coincidence trigger unit with power supply, and a computer with data acquisition software. MRI imaging was performed with the PET ring power off and on, using two representative MRI RF sequencing cases: T2 and MPRAGE.

The PET ring was placed around the brain phantom. Inside the PET ring was placed a standard Siemens 3T Flex Large flexible RF coil. The coil is large enough to cover most of the patient's head, leaving opening for the face. Imaging of the brain phantom was performed with and without the flexible coil. In the latter case, the whole body RF coil was used.

As previously described with respect to FIG. 1, for this example, the PET ring electronics are inside the RF shielded box placed on a plastic MRI compatible cart next to the end of the patient's table. In the first test, the electronics mobile cabinet was placed just outside the MRI room door with the flat cable going through the door. In the second and more practical variant, the cable connecting the PET ring electronics inside the MRI room and the cabinet in the operator room was exiting via the standard tube port provided in the wall connection panel. Inside the cabinet are housed the data acquisition system, the trigger module with power supply, and the computer/monitor.

Figure 20:
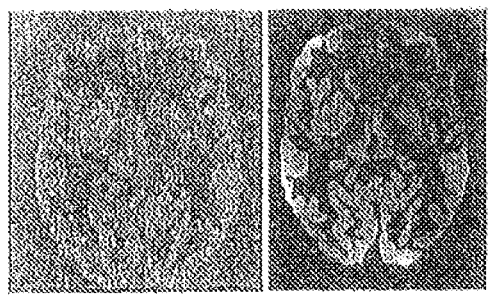
FIGS. 20A-B illustrate two MRI images taken by an exemplary ring PET, including 2 mm slices of the brain phantom using the MPRAGE RF pulse sequence.

FIGS. 20A-B illustrate two MRI images from the above example, namely, 2 mm slices of the brain phantom using the MPRAGE RF pulse sequence. FIG. 20A shows, for comparison, using the RF body coil only and with no power provided to the PET ring and the PET electronics/computer.

FIG. 20B shows using 3T Flex Large RF coil and with the PET ring and PET DAQ/computer system fully powered.

Figure 21:
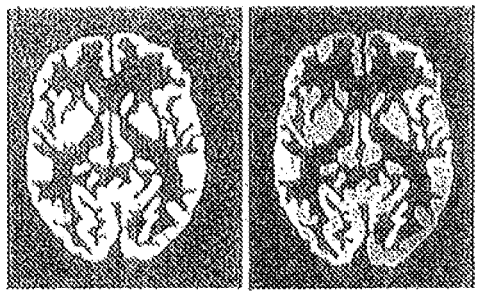
FIGS. 21A-B illustrate two MRI images taken by an exemplary ring PET, including 2 mm slices of the brain phantom using the T2 sequence.

FIGS. 21A-B illustrate two MRI images from the above example, namely, 2 mm slices of the brain phantom using the T2 sequence. FIG. 21A shows, for comparison, using the RF body coil only. FIG. 21B shows using 3T Flex Large RF coil. In both cases the PET ring and the PET DAQ/computer system was fully powered.

An exemplary imaging demonstration was performed with the PET ring insert imaging the brain PET phantom inserted inside the 3 Tesla MRI scanner. As before, a flex RF coil was used and inserted inside the PET ring, between the ring and the phantom. Sequential and simultaneous imaging sessions were performed, using T2 and MPRAGE sequences. The simultaneously obtained PET images, while RF sequences were run, showed signs of induced noise that needed to be filtered. However, sequentially obtained PET and MRI phantom images we were able to produced/obtained in the same setting.

Figure 22:
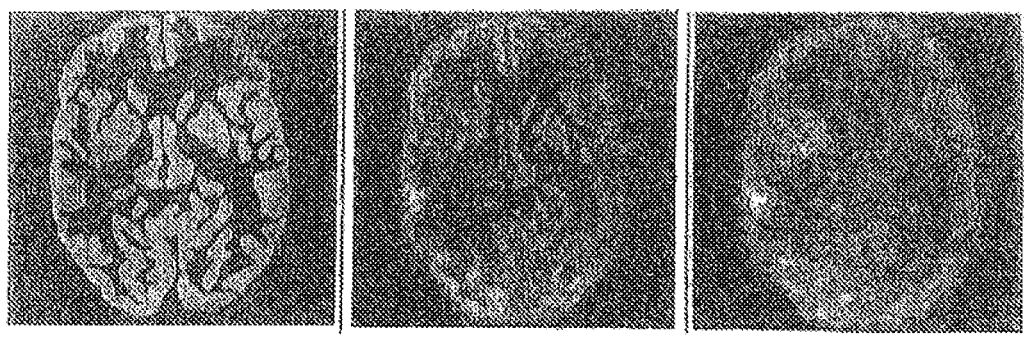
FIGS. 22A-C show dual modality imaging performed in a 3 Tesla MRI scanner in accordance with an exemplary demonstration of the present invention.

FIGS. 22A-C show dual modality imaging performed in the 3 Tesla MRI scanner of the exemplary demonstration. FIG. 22A shows a 2 mm T2 MRI slice image, while FIG. 22C shows a 1 mm PET slice image of the brain phantom. These two slice images of the brain phantom are shown overlaid in FIG. 22B. In this example, the PET image was collected for 10 minutes.

These pilot MRI tests described above prove that indeed simple means of using either: (1) only the whole body coil (for example: T2 sequence); or (2) using a standard flexible RF coil from the standard set of RF coils for the particular MRI scanner (for example: MPRAGE sequence and Siemens 3T Flex Large RF coil) can assure good signal-to-noise ("S/N") MRI imaging with the PET ring insert inside the bore of the MRI scanner. This evidence validates the novel non-standard approach described herein and opens the opportunity for the widespread implementation of economical hybrid PET/MRI imaging with a potential substantial impact on diagnostic imaging practice.

The position of the patient during MRI imaging can be, for example, supine (for example: brain, prostate, gynecological cancers, etc.), prone (for example: breast), but also upright (for example: patient sitting or standing during brain imaging) due to increasing availability of the inclined or vertical bore MRI scanners. MRI imaging in the upright position is enabling studies of the brain function that activates in the upright position. In addition to research, an example of clinical cases of interest is the study and assistance of the recovery in brains of stroke patients. The current inventive approach described herein is a relatively compact, lightweight wearable PET insert that can be "attached" mechanically and co-registered to the patient head, with a limited MRI-compatible mechanical support (to counterbalance the weight of the PET insert).

The PET/MRI combination can be also upgraded to a PET/EEG/MRI variant. Such hybrid imaging can be beneficial in the imaging, for example, of epilepsy patients or in other conditions with strong electrical abnormalities in their brains, in addition to increased brain research opportunities. The EEG electrodes, as usual, will be mounted directly on the head of the patient, with RF coils placed outside the EEG cap and inside the PET insert.

In the cases of prostate and OB/GYN PET imagers, in addition to the PET insert (with or without an endorectal or intra-vaginal PET probe), an optical modality can be also added to the PET/MRI combination.

In the case of pancreas imaging, an even smaller stomach inserted MR-compatible PET probe can be used and placed close (through the stomach wall) to the pancreas. The probe will operate with a set of panel detectors, as in the prostate and OB/GYN cases. This setup could also assist with other cases such as, for example, stomach cancers, etc.

The PET inserts of the present invention can also, in principle, possess high timing characteristics and, therefore, can operate in the Time of Flight ("TOF") mode with the advantage of improved S/N and higher image contrast.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

It should also be understood that all references identified and/or referenced herein are incorporated fully by reference herein in there entireties.

We claim:

1. A universal and portable Positron Emission Tomography (PET") insert for use with a Magnetic Resonance Imaging ("MRI") scanning device, the PET insert comprising:

a plurality of photodetector modules provided adjacent each other in an array, the plurality of photodetector modules configured for placement adjacent a body of a patient and sized to be received in a magnetic bore of the MRI scanning device with the patient, the photodetector modules providing detection of gamma annihilation photons;

a Radio Frequency ("RF") coil having a first end and a second end and provided between the patient and the plurality of photodetector modules, wherein each of the plurality of photodetector modules comprises a pixelated scintillator surrounding at least a portion of the patient's body, and a shielding block comprising silicon photomultiplier pads and passive electronic circuitry, and wherein the RF coil is a coil provided with the MRI scanning device with which the PET insert is used;

at least one front end amplifier positioned in said magnetic bore at a distance from said first or said second end of said RF coil, wherein said distance is within a range from 1 inch to 20 inches;

wherein the plurality of photodetector modules comprises a position-encoded, on-board analog readout comprising passive readout electronics wherein individual photodetector modules each have row and column outputs that are passively chained to form X and Y readout sectors in a single panel, wherein said position-encoded on-board analog readout is located in said PET insert and has a reduced number of analog channels exiting said PET insert as compared to a direct readout of each Silicon Photomultiplier pixels or Avalanche Photodiodes of said photodetector modules.

2. The PET insert of claim 1, wherein each shielding block includes silicon photomultiplier pads and passive electronic circuitry only.

3. The PET insert of claim 1, wherein the plurality of photodetector modules is formed as a ring for provision about a body part of the patient, and wherein the RF coil is provided about at least part of an annular range of the photodetector module ring.

4. The PET insert of claim 3, wherein the photodetector module ring comprises a plurality of rings stacked on top of each other forming a cylinder.

5. The PET insert of claim 3, wherein the photodetector module ring comprises a plurality of rings, at least some of the rings spaced apart from other rings for provision about different parts of a patient's body.

6. The PET insert of claim 1, wherein active components of the PET insert other than the silicon photomultiplier pads and said at least one front end amplifier, are disposed outside of the magnetic bore of the MRI scanner.

7. The PET insert of claim 1, wherein the RF coil extends past the edges of the plurality of photodetectors.

8. The PET insert of claim 1, wherein the RF coil comprises a whole body RF coil.

9. The PET insert of claim 1, wherein the plurality of photodetector modules is formed as a panel having an N×M array of photodetector modules.

10. The PET insert of claim 9, wherein the PET insert comprises at least two panels for provision against a patient's body in opposing relationship for imaging a desired portion of the patient's body.

11. The PET insert of claim 9, further comprising an endorectal PET probe operatively associated with the PET panel.

12. The PET insert of claim 1, wherein the photodetector modules include a scintillator as a sensor and energy converter of 511 keV annihilation gamma rays, and a photodetector to detect the scintillation light produced by the absorbed gamma rays in the scintillator.

13. A universal and portable Positron Emission Tomography ("PET") insert for use with a Magnetic Resonance Imaging ("MRI") scanning device, the PET insert comprising:
a plurality of photodetector modules provided adjacent each other in an array and formed as a ring for provision around a portion of a patient's body, the photodetector module ring sized to be received in a magnetic bore of the MRI scanning device with the patient, the photodetector modules providing detection of gamma annihilation photons;
a Radio Frequency ("RF") coil having a first end and a second end and provided between the patient and the plurality of photodetector modules, wherein the RF coil is provided about at least part of an annular range of the photodetector module ring, and wherein the RF coil extends over the edges of the photodetector module ring, wherein each of the plurality of photodetector modules comprises a pixelated scintillator surrounding at least a portion of the patient's body, and a shielding block comprising silicon photomultiplier pads and passive electronic circuitry only and wherein the RF coil is a coil provided with the MRI scanning device with which the PET insert is used; and
at least one front end amplifier positioned in said magnetic bore at a distance from said first or said second end of said RF coil, wherein said distance is within a range from 1 inch to 20 inches;
wherein the plurality of photodetector modules comprises a position-encoded, on-board analog readout comprising passive readout electronics wherein individual photodetector modules each have row and column outputs that are passively chained to form X and Y readout sectors in a single panel, wherein said position-encoded on-board analog readout is located in said PET insert and has a reduced number of analog channels exiting said PET insert as compared to a direct readout of each Silicon Photomultiplier pixels or Avalanche Photodiodes of said photodetector modules.

14. The PET insert of claim 13, wherein the photodetector module ring comprises a plurality of rings stacked on top of each other forming a cylinder.

15. The PET insert of claim 13, wherein the photodetector module ring comprises a plurality of rings, at least some of the rings spaced apart from other rings for provision about different parts of a patient's body.

16. A universal and portable Positron Emission Tomography ("PET") insert for use with a Magnetic Resonance Imaging ("MRI") scanning device, the PET insert comprising:
a plurality of photodetector modules provided adjacent each other in an array and formed as at least two panels for provision against a patient's body in opposing relationship for imaging a desired portion of the patient's body, the at least two photodetector module panels sized to be received in a magnetic bore of the MRI scanning device with the patient, the photodetector modules providing detection of gamma annihilation photons;
a Radio Frequency ("RF") coil having a first end and a second end and provided between the patient and the plurality of photodetector modules of each of the at least two panels, wherein the RF coil extends over the edges of the at least two photodetector module panels, wherein each of the plurality of photodetector modules comprises a pixelated scintillator array for surrounding at least a portion of the patient's body, and a shielding block comprising silicon photomultiplier pads and passive electronic circuitry only, and wherein the RF coil is a coil provided with the MRI scanning device with which the PET insert is used; and
at least one front end amplifier positioned in said magnetic bore at a distance from said first or said second end of said RF coil, wherein said distance is within a range from 1 inch to 20 inches;
wherein the plurality of photodetector modules comprises a position-encoded, on-board analog readout comprising passive readout electronics wherein individual photodetector modules each have row and column outputs that are passively chained to form X and Y readout sectors in a single panel, wherein said position-encoded on-board analog readout is located in said PET insert and has a reduced number of analog channels exiting said PET insert as compared to a direct readout of each Silicon Photomultiplier pixels or Avalanche Photodiodes of said photodetector modules.

17. The PET insert of claim 16, wherein each of the at least two panels has an N×M array of photodetector modules.

18. The PET insert of claim 16, further comprising an endorectal PET probe operatively associated with the at least two PET panels.

19. The PET insert of claim 16, wherein the plurality of photodetector modules is formed as a panel having an N×M array of photodetector modules and each photodetector module comprises the on-board analog readout configured as a charge division circuit.

\* \* \* \* \*